United States Patent [19]

Stone

[11] Patent Number: 5,364,792
[45] Date of Patent: * Nov. 15, 1994

[54] TEST SWAB AND METHOD OF MAKING AND USING SAME

[75] Inventor: Marcia J. Stone, Wellesley, Mass.

[73] Assignee: Hybrivet Systems, Inc., Natick, Mass.

[*] Notice: The portion of the term of this patent subsequent to Aug. 13, 2008 has been disclaimed.

[21] Appl. No.: 156,623

[22] Filed: Nov. 24, 1993

Related U.S. Application Data

[63] Continuation-in-part of Ser. No. 750,312, Aug. 27, 1991, abandoned, which is a continuation-in-part of Ser. No. 709,981, Jun. 4, 1991, abandoned, which is a continuation of Ser. No. 499,488, May 7, 1990, Pat. No. 5,039,618, which is a continuation-in-part of Ser. No. 305,221, Feb. 2, 1989, abandoned.

[51] Int. Cl.$^5$ .................... G01N 33/20; G01N 21/78
[52] U.S. Cl. ........................ 436/73; 436/77; 436/80; 436/81; 436/84; 436/169; 422/56; 422/58; 422/61
[58] Field of Search ........ 422/56, 57, 58, 61; 436/73, 76, 77, 80, 81, 84, 104, 169, 182; 128/759; 435/294, 295, 296

[56] References Cited

U.S. PATENT DOCUMENTS

| | | | |
|---|---|---|---|
| 1,753,301 | 4/1930 | Pitschner | 436/80 |
| 2,839,368 | 6/1958 | McConnaughey | 436/73 |
| 3,446,596 | 5/1969 | Salivar et al. | 23/230 |
| 3,509,872 | 5/1970 | Truhan | 128/2 |
| 3,741,727 | 6/1973 | Stroterhoff | 422/58 |
| 4,094,967 | 6/1978 | Gilbert | 424/28 |
| 4,166,765 | 9/1979 | Weetall | 435/26 |
| 4,184,483 | 1/1980 | Greenspan | 128/759 |
| 4,562,043 | 12/1985 | Mennen et al. | 436/66 |
| 4,707,450 | 11/1987 | Nason | 435/295 |
| 4,770,853 | 9/1988 | Bernstein | 422/58 |
| 4,804,518 | 2/1989 | Levine et al. | 436/66 |
| 4,824,789 | 4/1989 | Yafuso et al. | 436/68 |
| 4,873,197 | 10/1989 | Gould | 436/77 |
| 4,990,551 | 2/1991 | Haubl et al. | 524/30 |
| 5,009,845 | 4/1991 | Thoraval et al. | 436/104 |
| 5,039,618 | 8/1991 | Stone | 422/58 |
| 5,049,358 | 9/1991 | Lau | 422/56 |

FOREIGN PATENT DOCUMENTS

| | | |
|---|---|---|
| 3618842 | 12/1987 | Germany . |
| 2025047 | 1/1980 | United Kingdom . |
| 1481679 | 5/1989 | U.S.S.R. . |

OTHER PUBLICATIONS

Gov. Rep. Announce. Index (US) vol. 81, No. 6, 1981, p. 3375, B. Smuda, "Evaluation of applicability of a lead–sensitive test paper as a diagnostic tool . . . ".
*Chemical Analysis*, P. Elving et al, 1985, pp. 45–49, 112–113.
*Allied Fischer Scientific*, Fisher 86, pp. 496–497 (1985).
Rukmini et al., Talanta, vol. 26, pp. 579–580, 1979.
Nenova et al., Talanta, vol. 25, pp. 691–692, 1978.
Deshmukh et al., J. Indian Chem. Soc., vol. 29, No. 7, pp. 527–529, 1952.

*Primary Examiner*—James C. Housel
*Assistant Examiner*—Robert Carpenter
*Attorney, Agent, or Firm*—Burns, Doane, Swecker & Mathis

[57] ABSTRACT

A swab is impregnated with a test reagent such that a test for a specific substance can be effected by rubbing the impregnated swab over the surface to be tested and then viewing the swab for a reagent reaction. The swab may have a hollow stem, and within the hollow stem is a cartridge within another cartridge. An activator solution is in one of the cartridges and a reagent is in another of the cartridges. A method for testing for a substance includes impregnating a swab, and rubbing the swab over a surface suspected of containing the substance. If the substance is present in the surface, a reaction with the substance produces an easily detectable color on the swab tip.

24 Claims, 3 Drawing Sheets

TEST SWAB AND METHOD OF MAKING AND USING SAME

CROSS-REFERENCE TO RELATED APPLICATIONS

This application is a continuation-in-part application of application Ser. No. 07/750,312, filed Aug. 27, 1991, now abandoned which is a continuation-in-part of application Ser. No. 07/709,981, filed Jun. 4, 1991, and now abandoned, and which was a continuation of application Ser. No. 07/499,488, filed May 7, 1990, now U.S. Pat. No. 5,039,618,which was a continuation-in-part of application Ser. No. 305,221, filed Feb. 2, 1989, now abandoned.

TECHNICAL FIELD

The present invention relates to a swab and a method of using the swab in a test for certain chemical elements, and more particularly, the present invention relates to a swab for retaining test reagents, a method of using the same in a test for metals or other specific elements or compounds, and a method of making the same.

BACKGROUND OF THE INVENTION

Contamination of the environment has been increasing steadily for years as the use of metals, chemicals, pesticides, and bacterial organisms has increased. Even though the toxicity of various metals has been known for centuries, it is only recently that there has been a serious increase in interest in minimizing human exposure to such metals. Current public awareness of such pollutants and their associated hazards has created a consumer demand for products that are capable of determining the presence of unwanted and potentially dangerous materials.

Some of the more toxic metals include lead, cadmium, mercury, barium, chromium and beryllium. Lead, in particular, has been subject to much attention due to its presence in articles or paints commonly found in the home. See, for example, "A Simple Direct Estimation of Ultramicroquantities of Lead in Drinking Water Using Sodium Rhodizonate" by E. Jungreis and M. Nechama, *Microchemical Journal*, vol. 34, pp. 219–221 (1986); U.K. Patent Application No. 2 025 047 A; "A Simplified Method for Detection of Lead Contamination of Soil" by J. Preer and G. Murchison, Jr., *Environmental Pollution* (Series B), vol. 12, pp. 1–13; and "A Spot Test for Detection of Lead in Paint" by J. Sayre and D. Wilson, *J. Pediatrics*, vol. 46, pp. 783–785 (1970).

As the titles of some of the prior art publications indicate, there is a recognized need in the industry for a simple or simplified test or method for determining the presence of lead. However, as will become apparent from the remaining descriptions of the prior art, prior to the present invention, an effective and simple test for lead had not been developed.

In a popular prior art method of detecting lead in paint, sodium sulfide ($Na_2S$) is reacted with lead to form lead sulfide (PbS), a black precipitate. The presence of lead is thus confirmed by the appearance of the black precipitate, lead sulfide. This method has several disadvantages: (1) the sodium sulfide is potentially toxic, especially to young children; (2) the black precipitate is difficult to see on dark surfaces; (3) the sodium sulfide releases volatile hydrogen sulfide ($H_2S$), which has a noxious odor; and (4) the reagents react with many cations to form black precipitates and thus tends to give false readings on many metallic surfaces.

Another common analytical reagent is a metal complexing agent, rhodizonic acid. For over forty years, rhodizonic acid and salts thereof have been used as analytical reagents to detect heavy metals, including lead, in both qualitative and quantitative analyses. The methodology for using rhodizonate dye is based on two types of tests:

(1) a quantitative determination of heavy metals in solutions using a spectrophotometer to obtain quantitative information; and (2) qualitative determinations which use filter papers impregnated with the reagent.

In addition, semi-quantitative information can be derived from the use of columns packed with silica gel impregnated with rhodizonate dye. See U.K. Patent Application No. 2 025 047 A.

The Macherey-Nagel Company (Düren, Germany) manufactures a test paper for the determination of lead under the trademark PLUMBTESMO. The PLUMBTESMO strips comprise a heavy filter paper with a reagent impregnated therein. To test for lead in a solution, a strip is dipped into the solution, and observed for a color change that indicates the presence of lead. The PLUMBTESMO strips can also be used to detect lead deposits in motor vehicle tailpipes.

The instruction sheet that is distributed with the PLUMBTESMO strips indicates that the PLUMBTESMO strips may be used to detect the presence of lead on a degreased surface. However, the instruction sheet impliedly recognizes that the PLUMBTESMO strips are not entirely satisfactory for testing for the presence of lead on a surface. Specifically, the instruction sheet indicates that the PLUMBTESMO strip may have to be held firmly against a test surface for as long as fifteen minutes before an indication of lead develops. Clearly, for nonprofessional, household use, a test strip that must be held firmly for fifteen minutes is entirely unsatisfactory in that many users will become impatient after only a few minutes and will discontinue the application of the PLUMBTESMO strip against the test surface. That type of usage may, of course, result in dangerous false readings, leaving the user with the erroneous impression that lead is not present when in fact lead may be present.

A further disadvantage of the PLUMBTESMO strips is that the test operator must directly handle the test strips, thus being unnecessarily exposed to chemicals. Yet another disadvantage of the PLUMBTESMO strips is that the strips are flat and comparatively stiff, and are thus not readily conformable to curved or otherwise unusually contoured surfaces, such as those that one is likely to encounter on moldings in older houses.

Thus, it should be clear that the lead tests, known prior to the present invention, are not entirely satisfactory.

Although not a test for lead, U.S. Pat. No. 4,707,450 discloses a biological specimen collection and test unit. The teachings of U.S. Pat. No. 4,707,450 are quite different from the present invention. In summary, U.S. Pat. No. 4,707,450 discloses a specimen collection device that utilizes a swab to collect biological specimens for testing after the swab has been removed from the specimen collection location. Since lead and other metals do not readily collect on a swab when rubbed on a metal-containing surface, the disclosed swab is not useful for testing for metals. This is especially true because the success of the disclosed swab depends upon the removal of a specimen from the collection site for subsequent testing. Because metals will not usually collect on the swab, the swab will not work well for metals testing.

Thus, there is a need in the art for a test or method for determining the presence of toxic metals, such as lead and cadmium. While lead toxicity is better known, cadmium is toxic by inhalation of dust or fume and is a carcinogen. Cadmium plating of food and beverage containers has led to outbreaks of gastroenteritis or food poisoning. Other metals are just as toxic. Thus, a simple test for metals and other toxic substances would serve to protect consumers from the toxic effects caused thereby.

SUMMARY OF THE INVENTION

Briefly described, the present invention relates to a swab that is impregnated with a test reagent such that a test for a specific substance can be effected by rubbing the impregnated swab over the surface to be tested and then viewing the swab for a reagent reaction.

The present invention also relates to a device for testing for a substance on a surface including a cartridge, two compartments within said cartridge containing a reagent and an activating solution, respectively, and an absorbent ball of material mounted on at least one end of the cartridge. The reagent and activating solution are combined and mixed within the cartridge before the device is used.

The invention also relates to a method of making a device for testing a substance on a surface.

BRIEF DESCRIPTION OF THE DRAWINGS

The present invention may more easily be understood by reference to the drawings, wherein.

DETAILED DESCRIPTION OF PREFERRED EMBODIMENTS

The test swabs of the present invention may be used to detect a variety of substances on a variety of surfaces depending on the reagent contained in the swab, including but not limited to, paint, ceramics, dust, soil, plant leaves, solder, bird cages, etc. The test swabs may be used to determine the presence of lead, cadmium, bismuth, mercury, cobalt, arsenic, tin, antimony, iron, aluminum, selenium, copper or organophosphate, among others. The present invention preferably will be used to determine the presence of metals in such surfaces.

The swabs can be made in a variety of formats as shown in the Figures, which are described below.

Figure 1:
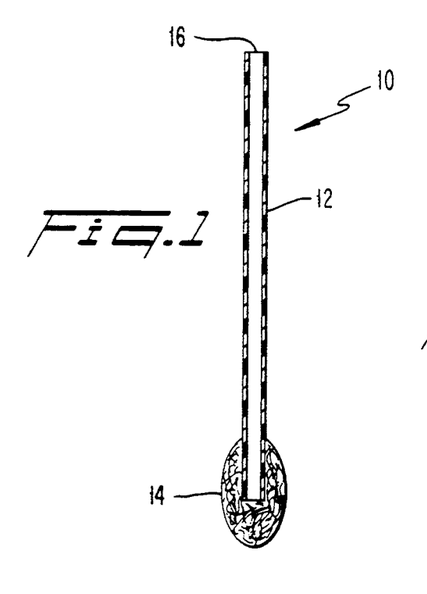
FIG. 1 is a view in cross section of a swab according to the present invention prior to the insertion of a reagent.
Figure 2:
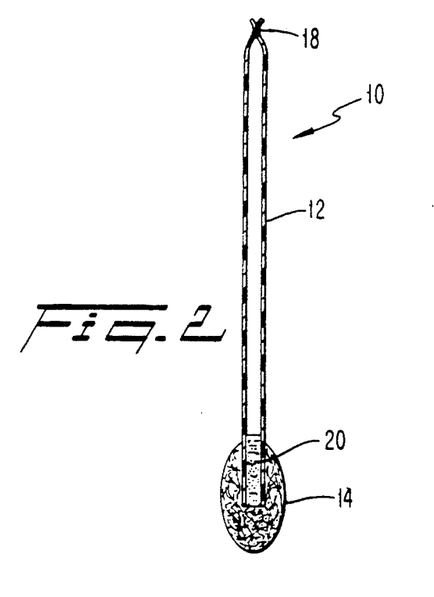
FIG. 2 is a view in cross section of a swab according to the present invention with a reagent inserted therein.

Referring now in detail to the drawings, wherein like reference numerals refer to like elements throughout, in the embodiments of FIGS. 1 and 2, a swab is indicated generally by reference numeral 10. The swab 10 includes a stem 12 that is preferably formed from a hollow tube. The stem 12 may be made from glass, plastic, or any other suitable material. If plastic is used, the composition of the plastic is not critical. However, because glass is breakable and because plastic is more easily crimped, plastic is preferable to glass.

In an alternative embodiment of the present invention, a solid stem may be used.

At one end of the stem 12, a ball 14 of absorbent material is affixed. The absorbent material may be comprised of any number of materials, including, but not limited to: cotton fibers, rayon fibers, dacron fibers, monofilament polyester, monofilament nylon, other fibrous polymeric compositions, or an open cell structure such as polyurethane foam. Table I lists several commercially available swabs, together with the source or manufacturer of each swab.

TABLE I

| ABSORBENT MATERIAL | APPROX. DIAMETER | STICK MATERIAL | STICK DIAMETER | SOURCE |
| --- | --- | --- | --- | --- |
| Cotton | 0.25" | Plastic | 3/16" | J & J |
| Cotton | 0.25" | Wood | Solid | CitMed |
| Cotton | 0.50" | Wood | Solid | CitMed |
| Rayon | 0.25" | Plastic | 3/16" | CitMed |
| Rayon | 0.50" | Plastic | 5/16" | CitMed |
| Dacron | 0.25" | Plastic | 3/16" | CitMed |
| Nylon | | | | Coventry |
| Polyester | 0.25" | Plastic | 3/16" | Coventry |
| Polyester/cellulose | | | | Coventry |
| Polyurethane | | | | Coventry |
| Porous Plastic | | | | Interflo |
| Foam dauber | | | | Metal Super Brush Co. |
| Wood dauber | 0.75" | | | Metal Nat'l Novelty Brush Co. |

For purposes of testing for lead, the preferred reagent dye is rhodizonic acid. Table II lists various dyes that are acceptable, together with the supplier or manufacturer of each.

TABLE II

| DYE | SUPPLIER |
|---|---|
| Rhodizonic acid, potassium salt | Sigma Chemical Company |
| Rhodizonic acid, sodium salt | Sigma Chemical Company |
| Rhodizonic acid, disodium salt | Sigma Chemical Company |

No major differences in purity or other analytical criteria were reported for similar salts. The above materials all function well in testing for the presence of lead, as indicated below. An activator solution, described below, typically will be used with the reagent dyes in carrying out embodiments of the present invention.

For purposes of testing for cadmium, the preferred reagent dyes are 4-nitronaphthalene-diazoamino-azobenzene or 1-(4-nitrophenyl)-3-(4-phenylazophenyl)-triazine. The latter dye may be obtained from Aldrich as Cadion.

Other substances may be tested for using the reagents and activating solutions listed in Table III.

TABLE III

| Metal | Dye (Reagent which Reacts with Metal) | Activating Solution | Color |
|---|---|---|---|
| Bi | Cinchonine - KI (1%) | Dilute acid | Orange Red |
| Hg | 1) Diphenylcarbazide (1% in alcohol) | 0.2 M HNO$_3$ | Violet |
|  | 2) Cobalt (II) thiocyanate test | Cobalt (II) acetate | Deep blue |
| Sb | 1) Rhodamine B (Tetraethylrhodamine) | Sb$^{+5}$ nitrite | Blue |
|  | 2) Phosphomolybdic acid | Sb$^{+3}$ | Blue |
| Fe | 1) 2,2'-bipyridine or 1,1' phenanthroline | Thioglycolic acid buffer | Red |
|  | 2) 3-(2-pyridyl)-5,6-bis(4-phenylsulfonic acid) | 1,2,4-triazine, sodium salt | Purple |
| Al | 1) Aurin tricarboxylic acid | NaOH | Red |
|  | 2) Quinolizarin | Ammonium, then glacial HONC | Red |
| Se | Pyrrole reagent | 0.5 M iron (III) chloride; H$_3$PO4 | Green-Blue |
| organophosphates | Phosphomolybdic acid formed with sodium molybdate | 1) K$_2$SO$_8$ + K$_2$SO$_4$ 2) Ascorbic Acid | Blue |
| Cu | 1) Quinolyl reagent (0.2 g/l in amyl alcohol) | 20 g Na acetate 10 g K Na tartrate 3 g hydroxylammonium Cl (all in 100 ml H$_2$O) | Red |
|  | 2) Dithiooxamide (1% in acetone) (Rubeanic acid) |  | Dark-Green |
| Co | Rubeanic acid | Ammonia/alkali tartrates | Brown |
| As | Magnesium nitrate/ammonium chloride | Silver nitrate | Red |
| Sn | Sodium sulfide | dilute acid | Brown (Sn$^{+2}$)/ Yellow (Sn$^{+4}$) |

Several granular and particulate solids were tried as diluents or fillers for the dyes to be used in the swabs. While fillers are not required, they are useful to provide bulk to the dye when the dye is a solid so the dye can be placed in the swabs more conveniently since the dye is used in a small amount. No filler is needed when the dye to be used is a liquid. The filler material may be any material which does not adversely affect the desired reaction. All of the materials listed in Table IV can be used as a filler for the dyes used in the test method of the present invention, but some exhibited more desirable properties than others. The more granular and less sticky solids are preferable to use with automatic filling equipment, such as a Kinematics Powder Filling Machine, model no. 1700 equipped with a model 3015 filling gun.

Table IV identifies several fillers and their ease of use with automatic filling equipment.

TABLE IV

| FILLER | RECOMMENDATION |
|---|---|
| Alumina, acid | Worked well with the machine and filling gun |
| Talc | Worked well with the machine and filling gun |
| Silicic acid | Formed a plug, but worked with the machine and filling gun |
| Glass beads | Formed a plug, but worked with the machine and filling gun |
| Polyvinylpyrrolidone | Not recommended for use with the filling equipment |

The rhodizonate dye is unstable in an aqueous medium. As a result, hygroscopic fillers may retain moisture too avidly and will consequently contribute to inactivation of this dye.

Table V identifies several materials capable of use as a filler for the dye, together with comments concerning the suitability of each material.

TABLE V

| BULKING AGENT | APPEARANCE | COMMENTS |
|---|---|---|
| Alumina -WB-2, basic |  | Loose, sandy; mixes well; fills tube easily |
| hygroscopic, |  |  |
| -WA-1, acidic | Loose | Mixes well; hygroscopic, fills tube easily |
| -WN-3, neutral | Loose | Mixes well; hygroscopic, fills tube easily |
| Bentonite |  | Particulate; colored powder; unsuitable for use |
| Cellulose |  |  |
| -SigmaCell 20 | Loose | Mixes well; fills tube easily |
| -SigmaCell 50 | Loose | Mixes well; fills tube easily |
| Florisil | Granular | Mixes poorly with days; fills tube easily |
| Fuller's Earth |  | Large pieces; particles too large to use |
| Fumed Silica | Fluffy | Too fluffy; mixes poorly; hard to use for filling |
| Glass Beads | Sandy | Mixes with dye poorly; fills tube easily |
| Gum Acacia | Loose | Mixes well; fills tube easily |
| Mannitol | Clumpy | Hygroscopic, dye mixes well |

TABLE V-continued

| BULKING AGENT | APPEARANCE | COMMENTS |
|---|---|---|
| Polyvinylpyrroli-done (PVP) | | Granular; mixes poorly; unsuitable for filling machine |
| Silicic Acid | Loose | Dye does not mix well; fills tube easily |
| Starch | | |
| -Potato* | Loose | Mixes well; turns dark; does not fill easily |
| -Wheat | Loose | Mixes well; does not fill tube easily |
| Talc | Powder | Mixes with dye moderately well fills tube easily |
| Zeolite | Fluffy Powder | Turns blue with the dye |
| Zeolite mixture | Fluffy Powder | Turns blue with the dye |

*Potato starch is susceptible to oxidation, and turns black on reaction with iodine. Rhodizonate reacts with potato starch as iodine does.

Accordingly, alumina (all types), talc, gum acacia, silicic acid, and mannitol are all suitable materials for use as a diluent with the dye. However, other materials in accordance with the spirit of the present invention may be used.

Figures 7, 8, 9, 10, 12, 13:
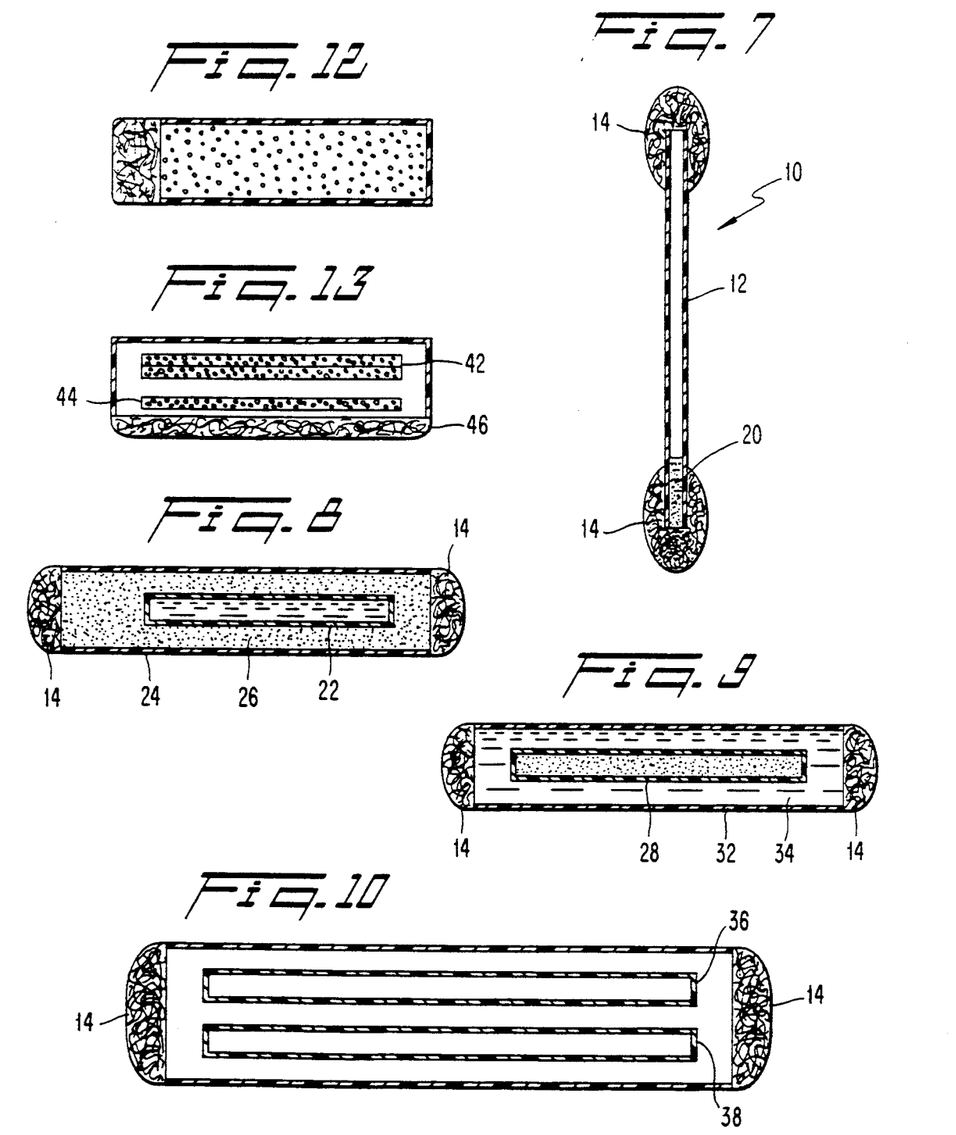
FIG. 7 is a view in cross section of a dual swab according to the present invention with a reagent inserted therein.
FIG. 8 is a view in cross section of a cartridge with a dual swab according to the present invention containing a cartridge and loose powder.
FIG. 9 is a view in cross section of a cartridge with a dual swab according to the present invention containing buffer and a cartridge containing dye.
FIG. 10 is a view in cross section of a cartridge with a dual swab according to present invention containing two cartridges side by side.
FIGS. 12 and 13 are views of embodiments of the present invention using microencapsulation.

The swabs 10 are filled through the open end 16 of the stem 12, preferably with automatic filling equipment, such as that described above. Once the desired quantity of dye and filler 20 is inserted into the swab 10, the end 16 of the stem 12 may be crimped as shown at 18 in FIG. 2. In the embodiment of FIG. 7, a ball of absorbent material 14 is inserted after the swab 10 is filled to provide a dual swab system.

In another embodiment, the swabs are filled with a dye/filler mixture using a Kinematics dispensing machine to fill. Then, the solid filled swabs are shaken on a vibrating table to disperse the solid throughout the swab. A four inch wooden applicator is inserted into the swab to prevent loss of reagent through the open end and a drop of glue from a glue gun then is applied to the end of the unit. In the dual swab embodiment of FIG. 7, an absorbent ball is added to the end of the swab.

Automatic filling units can be designed by using a metal brace notched with the appropriate size holes to ensure that the swabs remain in a fixed position during an automatic filling operation. A conveyor belt can move these units under a fixed dispensing gun. After the dispensing of the solid reagent, the swabs can be sealed by a variety of automatic procedures including, melting to close, using pressure to close and flattening the plastic handle of the swab.

In various tests, swabs were filled with 20, 30, 40, and 80 mg. of the dye and filler. In such tests, the ratios of filler to dye were varied between 0 and 100:1.

In use, the absorbent ball 14 of the filled swab 10 is wetted with an activator solution. A pH level of between about 2.0 and about 3.0 is preferable for the lead-rhodizonate reaction. For the lead reaction, a buffer generally is used as the activator solution. A pH level of 2.8 for the buffer is optimal for the lead-rhodizonate reaction. The wetted absorbent ball 14 is then rubbed onto a surface suspected of containing lead. If lead is present on the surface, a reaction occurs with the rhodizonate dye, thus causing an easily detectable deep pink color to appear on the absorbent ball 14 of the swab 10. The test is even sensitive enough to detect lead dust on a surface caused by sanding lead-containing paint, even after the surface had been vacuumed and washed with trisodium phosphate detergent.

For the cadmium reaction, the activator solution generally will comprise sodium tartrate, sodium acetate, sodium citrate, potassium hydroxide or a mixture thereof. Additional chelating materials such as EDTA may also be present. The pH preferably used for the cadmium reaction is above about 8, more preferably above 9. The potassium hydroxide may be used to adjust the pH. Bases other than hydroxide, which form insoluble cadmium complexes, such as carbonate, might be used. When testing for cadmium, the area to be tested is rubbed with the swab containing the reagent and activator solution. If the swab becomes pink, cadmium is present.

The pH to be used with detection of other metals and substances will be readily determined by one of ordinary skill in the art from the reagents and activating solutions disclosed in Table III and the Examples below.

Interferences Caused By Other Cations

Many cations form complexes with rhodizonate. However, the specific conditions for optimal reaction of most cations are different from those required for lead. Only barium and lead form a red or deep pink complex under the conditions defined for the swab tests. The color formed by the reaction with barium is red-brown and thus to a skilled technician is distinguishable from the color formed during the reaction with lead. However, to avoid confusion, the reaction with barium can be distinguished from the reaction with lead with the use of sodium sulfide. A drop of sodium sulfide (7.5%) on top of the developed pink swab changes the swab to black in the presence of lead by forming lead sulfide. The precipitate formed by the reaction between sodium sulfide and barium is not black, i.e., sodium sulfide does not change to black in the presence of barium alone.

The solid fill method, described above with the use of a Kinematics filling machine, is the manufacturing option that is best for preserving the stability of the dye reagent. However, alternative manufacturing protocols are also available.

In an alternative method of preparation of a swab for a lead test, an aqueous solution of 0.01M rhodizonate (dye) is prepared. The rhodizonate solution may be prepared using a tartrate buffer at pH 2.8. Although that pH level is the preferred level for the lead testing reaction, at that pH level, the rhodizonate dye is unstable and completely degrades in about thirty-six hours. As an alternative, the rhodizonate solution can be prepared using water at pH 5 or 6. At that pH level, complete degradation of the rhodizonate takes about ninety-six hours.

The addition of some organic solvents may enhance the stability of the aqueous rhodizonate solution. For example, 10 to 20% methanol, ethanol, or acetone may be added.

Within one hour of preparation of the solution, swabs are dipped in the solution for thirty seconds to one minute. The swabs are then rapidly frozen in acetone/dry ice, or liquid nitrogen, and dried by lyophilization. The swabs can then be used in the same manner as the swabs that are filled from the inside with a filling machine. The swabs can alternatively be dried under heat, although the temperature must be kept below 80° C.

In another embodiment, the swabs can be pretreated by soaking the absorbent material of the swabs in a tartrate buffer, pH 2.8, or any other buffer with a pH preferably between 2 and 3. The soaked swabs are then dried under heat.

Since other cations might interfere with a test for lead, the swab can also be presoaked in a buffer containing EDTA for about one minute in order to clean other possible interfering cations from the swab prior to the test. The EDTA can be included in the buffer described in the preceding paragraph.

In one preferred embodiment, the swab of the present invention is prepared as a cartridge swab. In this embodiment, a device for testing for a substance or metal on a surface comprises a cartridge, at least two compartments within the cartridge wherein one compartment contains a reagent that reacts with the metal and the other compartment contains an activating solution, and an absorbent ball of material mounted at least one end of the cartridge. The reagent and activating solution are combined and mixed within the cartridge before the device is used. This embodiment can take several forms, some of which are shown in FIGS. 3–6, 8–11, and 14–15.

The simplest design of the cartridge swab is a system wherein two compartments are used. One compartment contains an activator solution and the other contains a dye. When testing for lead, the activator solution will be the buffer solution described above and the dye will be rhodizonate dye. When testing for cadmium, the activator solution will be sodium tartrate, sodium acetate, sodium citrate, potassium hydroxide or mixtures thereof, and the dye will be 4-nitronaphthalene-diazoamino-azo-benzene or 1-(4-nitrophenyl)-3-(4-phenylazophenyl)triazine. The absorbent ball mounted at one end of the cartridge swab may be attached when the cartridge swab is prepared or it may be attached when the cartridge swab is to be used. Where there is an absorbent ball at each end of the cartridge swab, one end is closed with an absorbent ball, the cartridge swab is filled and then the other absorbent ball is attached when the cartridge swab is prepared or when it is to be used.

Figures 3, 4, 5:
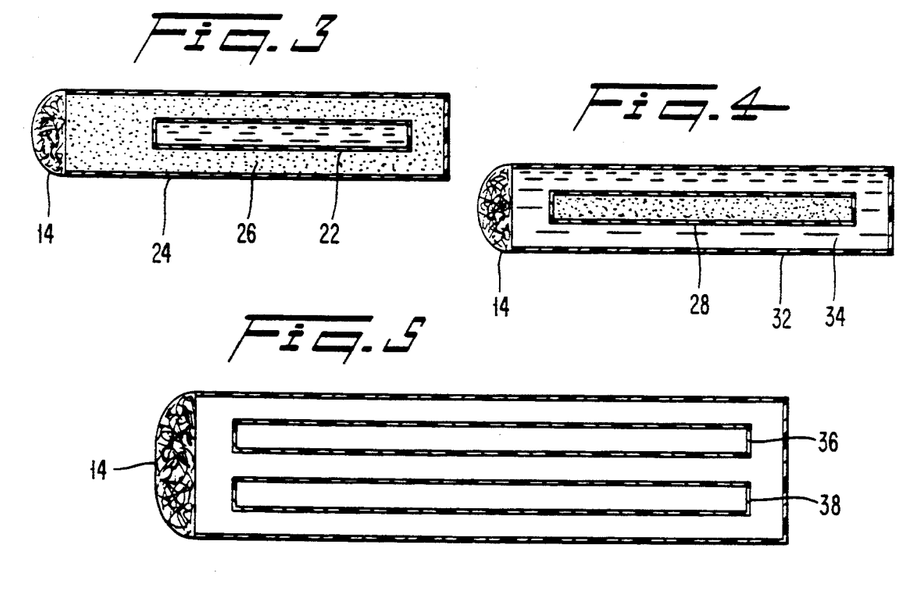
FIG. 3 is a view in cross section of a cartridge swab according to the present invention containing a cartridge and loose powder.
FIG. 4 is a view in cross section of a cartridge swab according to the present invention containing buffer and a cartridge containing dye.
FIG. 5 is a view in cross section of a cartridge swab according to the present invention containing two cartridges side by side.

FIG. 3 shows an embodiment of a cartridge swab wherein a breakable cartridge 22 contains a small amount of activator solution. The breakable cartridge 22 is inserted into a plastic holder or cartridge 24 into which dry dye powder 26 plus any additives required for the test desired has been dispensed. The swab tip 14 generally will be placed on the cartridge 24 before the cartridge 24 is filled with dry dye powder 26 and the breakable cartridge 22. When the cartridge swab is to be used, the breakable cartridge 22 is broken and the activator solution mixes with the dye powder and wets the swab tip. The swab tip then can be rubbed over the surface to be tested. As shown in FIG. 8, this embodiment may also be utilized in the dual swab configuration.

FIG. 4 shows an embodiment of a cartridge swab wherein a small breakable cartridge 28 is prepared containing dry dye powder plus any additives required for the desired test. The cartridge 28 is placed inside another breakable cartridge 32 large enough to hold cartridge 28 and sufficient activating solution 34 to execute the desired test. The breakable cartridge is broken when the test is to be performed and the activating solution mixes with the dye and wets the swab tip which can be rubbed over the surface to be tested. As shown in FIG. 9, this embodiment may also be utilized in the dual swab configuration.

FIG. 5 shows an embodiment of the cartridge swab wherein two breakable cartridges are used side by side in a larger cartridge. Breakable cartridges 36 and 38 will contain either activating solution or dye. The cartridges are broken together when the test is to be performed and the activating solution mixes with the dye and wets the swab tip which can be rubbed over the surface to be tested. As shown in FIG. 10, this embodiment may also be utilized in the dual swab configuration.

Figure 6:
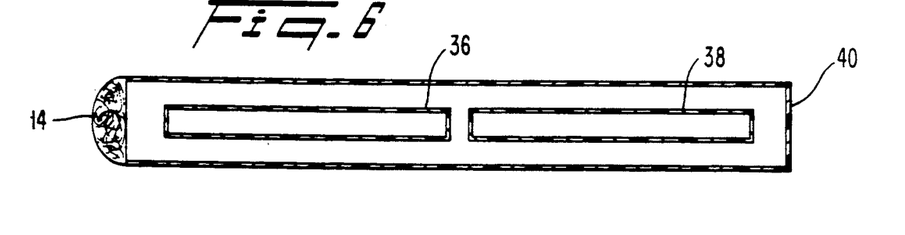
FIG. 6 is a view in cross section of a cartridge swab according to the present invention containing two cartridges end to end.
Figure 11:
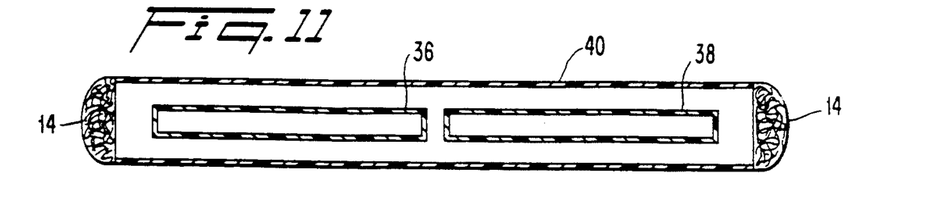
FIG. 11 is a view in cross section of a cartridge with a dual swab according to the present invention containing two cartridges end to end.

FIG. 6 shows an embodiment of the cartridge swab wherein two breakable cartridges 36 and 38 are used in an end to end format inside a larger cartridge 40 which has a swab tip 14. The cartridges are broken together when the test is to be performed and the activating solution mixes with the dye and wets the swab tip which can be rubbed over the surface to be tested. As shown in FIG. 11, this embodiment may also be utilized in the dual swab configuration.

In the dual swab embodiments of FIGS. 8–11, the compartments must contain enough reagent and activating solution to wet the absorbent balls at each end of the cartridge swab. This may require using an additional amount of each reagent in the cartridges over the amount needed for the monoswab embodiments. One of ordinary skill in the art will readily be able to ascertain the amounts needed for a dual swab cartridge from the examples below for the monoswab embodiments.

Figure 14:
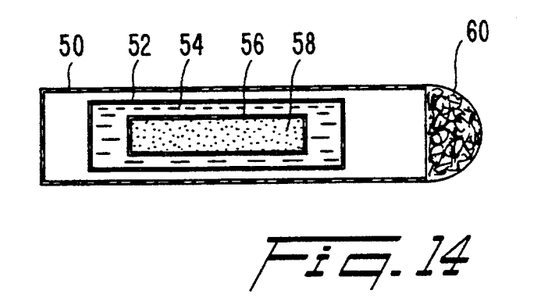
FIG. 14 is a view of an embodiment having a cartridge within a cartridge.

FIG. 14 is a view of an embodiment of a cartridge swab having a stem 50 and a swab tip 60. Inside the stem 50 is a breakable cartridge 52, which contains a small amount of activator solution 54. The breakable cartridge 52 also includes a smaller breakable cartridge 56 inside the cartridge 52. The inner cartridge 56 includes a dye 58, such as a dry dye powder, plus any additives that might be required. When the swab is to be used, the cartridges 52, 56 are broken and the activator solution mixes with the dye inside the stem 50 and wets the swab tip 60. The swab tip 60 then can be rubbed over the surface to be tested. This embodiment may also be utilized in the dual swab configuration, wherein a swab tip is placed at each end of the stem 50.

Figure 15:
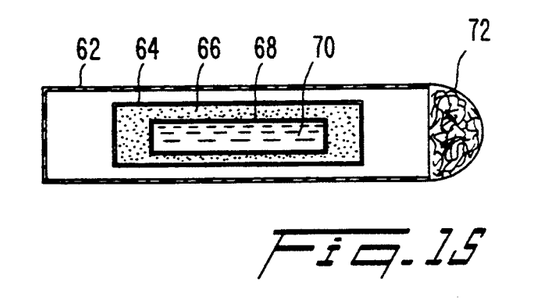
FIG. 15 is a view of another embodiment having a cartridge within a cartridge.

FIG. 15 is a view of an embodiment of a cartridge swab having a stem 62 and a swab tip 72. Inside the stem 62 is a breakable cartridge 64, which contains a small amount of dye 66, such as a dry dye powder, plus any additives that might be required. The breakable cartridge 64 also includes a smaller breakable cartridge 68 inside the cartridge 64. The inner cartridge 64 includes an activator solution 70. When the swab is to be used, the cartridges 64, 68 are broken and the activator solution 70 mixes with the dye inside the stem 62 and wets the swab tip 72. The swab tip then can be rubbed over the surface to be tested. This embodiment may also be utilized in the dual swab configuration, wherein a swab tip is placed at each end of the stem 62.

The activator solution and the reagents used in the embodiments disclosed in FIGS. 14 and 15 may be any of those disclosed herein, or any other suitable materials generally known to those of ordinary skill in the art.

In a further embodiment, more than two compartments are provided to allow the necessary amount of reagent and activating solution to be present in the cartridge swab. For example, four cartridges may be used to supply the necessary reagent and activating solution to each end of the cartridge swab.

In a further embodiment of the present invention, only one end of the cartridge is closed with an absorbent ball and the other end of the cartridge is closed with abrasive paper or board material. This embodiment is preferred for use on surfaces which need to be roughened in order to get good contact between the absorbent ball and the surface. The cartridge swab can be used to first roughen the surface with the abrasive paper, and then test the surface for a substance or metal with the end of the cartridge swab having an absorbent ball.

The swab tips on the cartridge swabs can be the same type of swabs described above for use on the stick type swabs.

The cartridges which are used to hold the breakable cartridges containing the reactants for the desired test can be nonbreakable or squeezable containers. For example, a squeezable cartridge similar to a toothpaste tube may be used. The breakable cartridges are placed inside the squeezable cartridge and the end is closed with a fibrous or porous swab tip. The swab tip optionally may have a pointed tip which breaks the cartridges contained within the tube. The squeezable cartridge is squeezed, breaking the cartridges within the squeezable cartridge and mixing the reagents. The reagents wet the swab tip which can then be rubbed over the surface to be tested.

The breakable or squeezable cartridges contained within the cartridge swabs may be glass, plastic or other material which will open upon crushing or squeezing. Where glass cartridges are used, the unit will preferably contain spacers between the cartridges to prevent premature breakage of the glass cartridges, allowing reagents to mix prior to the desired time for use. When plastic cartridges are used, any type of plastic which will open on application of pressure is satisfactory. This plastic may be rigid and brittle, such as butyrate tubing, polymethyl pentene or polystyrene or flexible, such as low density polyethylene, polyallomer, or polyvinyl chloride. Flexible plastic containers are advantageous since there is no glass to break and no pieces of glass which may come through the outer package. Such flexible plastic cartridges may be sealed using an ultrasonic sealing technique so that gentle pressure will break the seals opening the reagent cartridges, releasing the materials contained inside.

The test swabs are preferably packaged in test kit packets which include at least one and, more preferably, several swabs. For test kits for lead, the test kit will preferably also contain a control tube filled with sodium sulfide. As discussed above, sodium sulfide reacts with many cations to form black precipitates and may give false readings when used as a test for lead. However, it has been found useful to include a control tube containing sodium sulfide in the test kits for lead in order to enable the user of the test kit to double check the results of the other test swabs. The inclusion of a sodium sulfide control may also be useful where the user desires to test for lead on plaster and stucco surfaces. Since these materials may contain sulfates, the reagents used in the test swabs according to the present invention may be blocked from reacting with lead in the plaster or stucco surface to produce a visible reaction. The sodium sulfide tube is provided to allow the user to check these surfaces with the same kit as used for other surfaces.

In one preferred embodiment, the test kit will contain an insert card which has been coated in at least one area with a lead or other metal-containing material. For example, a cardboard or paper board insert may be prepared with one or more circles or patches of lead or other metal-containing material coated thereon. If a user of the test kit obtains negative results with the test swabs in the kit when the swabs are applied to the surface of interest, the user can rub the swabs over the areas of metal-containing material on the insert card to verify the accuracy of the test. If the swabs indicate the presence of lead or other metal when contacted with the card containing such material, the user is assured that the negative results obtained were correct.

The test kit according to the present invention comprises at least one device for testing for a substance on a surface, comprising a cartridge, at least two compartments within the cartridge wherein at least one compartment contains a reagent that reacts with the substance and at least one other compartment contains an activating solution, and an absorbent ball of material mounted at at least one end of the cartridge. The reagent and activating solution are then combined and mixed within the cartridge before the device is used.

In a preferred embodiment, the test kit further comprises at least one tube for dispensing sodium sulfide. The tube for dispensing sodium sulfide may be any type of tube or dropper for dispensing materials. Preferably, the tube will be a test swab according to the present invention.

In a preferred embodiment, the test kit further comprises an insert card coated in one or more areas with the substance for which the kit is intended to test. The insert card may by cardboard, paper board or any other material capable of being coated with the desired material.

As an alternative to the embodiments using one or two cartridges, there can be a plurality of compartments containing reagents. In one embodiment, the compartments are micro-compartments such as those formed by microencapsulation. The micro-compartments can be formed by any method known to those of skill in the art of microencapsulation. See FIG. 12.

FIG. 13 illustrates another embodiment utilizing microencapsulation having a liquid layer 42, a solid layer 44, and a liquid permeable absorbent pad, 46. In a further embodiment, the liquid layer and the solid layer may be reversed.

The following examples are provided to further illustrate the invention, but are not meant to limit the scope of the invention in any way.

EXAMPLES

Tests To Determine Preferred Ratios Of Filler To Dye

Examples I Through XIII

In examples I through XIII, swabs were obtained from CitMed having an absorbent ball of 0.50 inch diameter made from rayon fibers. The swab stem was a 3/16 inch hollow plastic tube. Alumina (WA-1, acidic) was used as an inert diluent, and rhodizonate dye, disodium salt (from the Sigma Chemical Company) was used as the dye. The inert diluent was mixed with the dye in the ratios set forth in Table V. Table V also lists the quantity of fill used in the swab, together with the test results.

In performing the above examples, the swabs, after being filled with the above-designated quantities of the above-designated ratios of filler and dye, were wetted with 1.5 ml. of 0.2M tartrate buffer, pH 2.8. The swabs were then rubbed on wood that had been previously painted with 0.5% lead-containing paint. In most instances, a positive reaction was clearly visible within seconds, almost always within less than one minute. A positive reaction is indicated by a deep pink color appearing on the absorbent ball of the swab.

TABLE VI

| RATIO ALUMINA:DYE | FILL (mg) | REACTIVITY |
|---|---|---|
| 100:1 | 40 | All positive |
| 100:1 | 80 | All positive |
| 80:1 | 40 | All positive |
| 80:1 | 80 | All positive |
| 60:1 | 40 | All positive |
| 60:1 | 80 | All positive |
| 40:1 | 30 | All positive |
| 40:1 | 40 | All positive |
| 40:1 | 80 | All positive |
| 20:1 | 40 | All positive |
| 20:1 | 80 | All positive |
| 10:1 | 40 | 50% positive-too much dye |
| 5:1 | 40 | no reaction-too much dye |

Example XIV

A mixture of alumina (acidic) and rhodizonate dye, sodium salt at a ratio of 40:1 was suspended in 0.2M tartrate buffer, pH 2.8. The following swabs: cotton, 6" plastic rod, from CitMed; rayon, 6" plastic rod, from CitMed; and dacron, 6" plastic rod, from CitMed, were individually dipped in the suspension. The dipped swabs were then rubbed on a piece of wood painted with a 0.5% lead-containing paint. The suspension lost activity rapidly, losing its ability to detect lead within one minute. It is interesting to note that the suspension lost activity more rapidly when soaked onto the swab, as in this example, than when the mixture was filled through the center of the swab and then wetted with the buffer.

Example XV

A mixture of alumina (acidic) and rhodizonate dye, sodium salt at a ratio of 20:1 was suspended in 0.2M tartrate buffer, pH 2.8. The following swabs: cotton, 6" plastic rod, from CitMed; rayon, 6" plastic rod, from CitMed; and dacron, 6" plastic rod, from CitMed, were individually dipped in the suspension. The dipped swabs were then rubbed on a piece of wood painted with a 0.5% lead-containing paint. The suspension decayed at a rate slower than the suspension used in example XIV. Activity was still observed after five minutes.

Example XVI

A mixture of mannitol and rhodizonate dye, sodium salt at a ratio of 20:1 was suspended in 0.2M tartrate buffer, pH 2.8. The following swabs: cotton, 6" plastic rod, from CitMed; rayon, 6" plastic rod, from CitMed; and dacron, 6" plastic rod, from CitMed, were individually dipped in the suspension. The dipped swabs were then rubbed on a piece of wood painted with a 0.5% lead-containing paint. The suspension decayed at a rate slower than the suspension used in example XIV. Activity was still observed after five minutes.

Tests To Determine Sensitivity Of Reagent

Example XVII

To determine the sensitivity of the test, a contoured wood molding strip was divided into ten different sections. Each section was painted with latex paint that was mixed with a different quantity of lead, ranging from 0.1% to 1.0%. The following diagram illustrates the various ratios used:

0.1% 0.2% 0.3% 0.4% 0.5% 0.6% 0.7% 0.8% 0.9% 1.0%

A swab with a 0.5 inch diameter absorbent ball made from rayon fibers and a 5/16 inch hollow plastic stem was filled with 40 mg. of alumina (WA-1, acidic) and rhodizonate dye, disodium salt (from the Sigma Chemical Company) in a 40:1 ratio. A 1.5 ml. solution of 0.2M tartrate buffer, pH 2.8 was used as the developing agent. Within less than thirty seconds, a deep red color developed on the swab after rubbing the treated swab on the wood section painted with 0.4% lead-containing paint. Similarly treated swabs had equal or better results on all sections of the wood having a higher percentage of lead in the paint.

Tests To Compare Results Of Swab With Results Of Filter Paper

Example XVIII

For comparison with the swab test set forth in example XVII above, a similar test was conducted using Whatman 3 mm. filter paper. A solution was prepared using 40 mg. of alumina (WA-1, acidic) and rhodizonate dye, disodium salt (from the Sigma Chemical Company) in a 40:1 ratio and a 1.5 ml. solution of 0.2M tartrate buffer, pH 2.8. The filter paper was dipped into the solution, allowing the solution to completely saturate the filter paper. The saturated filter paper was then promptly rubbed over the wood painted with lead-containing paint.

The filter papers never clearly turned pink even when used on the sections of wood having high concentrations of lead. Hints of pink were occasionally visible at the edges of the filter paper; however, interpretation was very difficult. The wood underneath the filter paper did become pink, but this pink color was only visible on the light colored paint, not on the dark paint. On the contoured wood surfaces it was difficult to make good contact between the filter paper and the contoured surfaces.

Example XIX

A swab with a 0.5 inch diameter absorbent ball made from rayon fibers and a 5/16 inch hollow plastic stem was filled with 40 mg. of alumina (WA-1, acidic) and rhodizonate dye, disodium salt (from the Sigma Chemical Company) in a 40:1 ratio. A 1.5 ml. solution of 0.2M tartrate buffer, pH 2.8 was used as the developing agent, i.e., the swab was prepared exactly as set forth in example XVII, above. This time the swab was rubbed on lead-glazed ceramic dishes. Within less than thirty seconds, the tip of the swab was obviously pink.

Example XX

A solution was prepared using 40 mg. of alumina (WA-1, acidic) and rhodizonate dye, disodium salt (from the Sigma Chemical Company) in a 40:1 ratio and a 1.5 ml. solution of 0.2M tartrate buffer, pH 2.8. A piece of Whatman 3 mm. filter paper was dipped into the solution, allowing the solution to completely saturate the filter paper, i.e., the filter paper was prepared in accordance with the method set forth above in example XVIII. The treated filter paper was rubbed on the lead-glazed ceramic dishes used in example XIX. No detectable color was observed on the filter paper after several minutes of contact with the lead-glazed dishes.

Example XXI

Plain untreated swabs having a rayon fiber absorbent ball of 0.5 inch diameter on a 5/16 inch hollow plastic stem were soaked in a solution of 40 mg. of alumina (WA-1, acidic) and rhodizonate dye, disodium salt (from the Sigma Chemical Company) in a 40:1 ratio and a 1.5 ml. solution of 0.2M tartrate buffer, pH 2.8, i.e., the same solution used in examples XVIII and XX. When the swabs were then rubbed on the lead-glazed ceramic dishes, a clear positive result was easy to read.

Example XXII

Plain untreated swabs having a rayon fiber absorbent ball of 0.5 inch diameter on a 5/16 inch hollow plastic stem were soaked in a solution of 40 mg. of alumina (WA-1, acidic) and rhodizonate dye, disodium salt (from the Sigma Chemical Company) in a 40:1 ratio and a 1.5 ml. solution of 0.2M tartrate buffer, pH 2.8, i.e., the same solution used in examples XVIII, XX, and XXI. When the swabs were then rubbed on the wood painted with at least 0.4% lead-containing paint, a clear positive result was easy to read.

From the results of examples XVII through XXII, it is clear that the swab is far superior to the filter paper for effecting a test for the presence of lead using rhodizonate dye.

Comparison Of Different Types Of Swabs

Example XXIII

A mixture of alumina (acidic) and rhodizonate dye, sodium salt at a ratio of 40:1 was filled into the following swabs: cotton, 6" plastic rod, from CitMed; rayon, 6" plastic rod, from CitMed; and dacron, 6" plastic rod, from CitMed. About 3/16" to ¼" of material was filled in each swab. The swabs were then wetted with tartrate, sodium salt and rubbed on a wood board painted with a 0.5% lead-containing paint.

There were no notable differences in color intensity among the swabs made of cotton, rayon, or dacron. The dacron and rayon swabs wetted well, whereas the first few drops of buffer beaded on the surface of the cotton. During the rubbing stage, the dacron swab did not hold up as well as the cotton and rayon swabs.

Example XXIV

A mixture of mannitol and rhodizonate dye, sodium salt at a ratio of 20:1 was suspended in 0.2M tartrate buffer, pH 2.8. The following swabs: cotton, 6" plastic rod, from CitMed; rayon, 6" plastic rod, from CitMed; dacron, 6" plastic rod, from CitMed; molded foam from Coventry Mfg. Co.; spun foam from Coventry Mfg. Co.; and 3" cotton tipped swabs from Johnson & Johnson, were individually dipped in the suspension. The dipped swabs were then rubbed on a piece of wood painted with a 0.5% lead-containing paint. The foam materials did not wet well, and little or no color formation was observed on the material or the wood. The cotton, rayon, and dacron swabs had intense color on the fibers. Under a microscope it appeared that the fibers had been dyed. It did not appear as though a precipitate had been formed and trapped by the fibers. However, at high concentrations of lead and dye, some precipitate may form. The precipitate is not necessary in order to detect a reaction.

The size of the absorbent ball on the swab also had little apparent effect on the test results.

Example XXV

A swab with a hollow stem is filled with 30 mg of a mixture of 4-nitronaphthalene-diazoamino-azobenzene and an inert filler, alumina in ratios as shown in Table VI. The swab tip is wetted with an activator solution containing sodium potassium tartrate, sodium acetate, or sodium citrate at pH 8.5. The area to be tested is rubbed with the swab. If cadmium is present, the swab becomes pink.

Example XXVI

One crushable cartridge is filled with 30 mg Cadion, (1-(4-nitrophenyl)-3-(4-phenylazophenyl)triazine) and talc. Another breakable cartridge is filled with 0.5 ml activator solution which is a mixture of sodium tartrate, sodium acetate and sodium hydroxide. The pH of the activator solution is adjusted to be basic at a pH greater than 9.

The two cartridges are placed inside a larger cartridge having a swab tip at one end. When ready to use, the breakable cartridges are broken and the unit is shaken to ensure good mixing. The swab tip is rubbed over the area to be tested and becomes pink if cadmium is present.

Tests For Other Materials

Example XXVII

A swab with a hollow stem is filled with 30 mg of a mixture of cinchonine-potassium iodide reagent and an inert filler such as alumina in ratios as shown in Table VI. The swab tip is wetted with an activator solution containing dilute acid such as 0.1M $HNO_3$ at pH 2–3. The area to be tested is rubbed with the swab. If bismuth is present, the swab turns orange-red.

Although the salts of lead, copper and mercury react with iodide and hence interfere with the reaction with bismuth, bismuth can be detected in the presence of these metal salts.

Example XXVIII

One breakable compartment is filled with 30 mg of cinchonine-potassium iodide and an inert filler such as talc. Another breakable compartment is filled with 0.5 ml of activator solution containing dilute acid such as 0.1M $HNO_3$ adjusted to pH 2.

The two cartridges are placed inside a larger cartridge having a swab tip at one end. When ready to use, the compartments are broken open and the unit is shaken to ensure good mixing. The swab tip is rubbed over the area to be tested and becomes orange-red if bismuth is present.

Although the salts of lead, copper and mercury react with iodide and hence interfere with the reaction with bismuth, bismuth can be detected in the presence of these metal salts.

Example XXIX

A swab with a hollow stem is filled with 30 mg of a mixture of diphenyl carbazide and an inert filler such as alumina in ratios as shown in Table VI. The swab tip is wetted with an activator solution containing 0.2M $HNO_3$ in 6% ethanol. The area to be tested is rubbed with the swab. If mercury ($Hg^{+2}$) is present, the swab turns violet.

Example XXX

One crushable cartridge is filled with 30 mg of a mixture of diphenyl carbazide and an inert filler such as talc. Another breakable cartridge is filled with 0.5 ml of activator solution containing 0.2M $HNO_3$ in 6% ethanol. The two cartridges are placed inside a larger cartridge having a swab tip at one end. When ready to use, the breakable cartridges are broken and the unit is shaken to ensure good mixing. The swab tip is rubbed over the area to be tested and becomes violet if mercury ($Hg^{+2}$) is present.

Example XXXI

A swab with a hollow stem is filled with 30 mg of a mixture of ammonium thiocyanate, cobalt (II) acetate and an inert filler such as alumina in ratios as shown in Table VI. The swab tip is wetted with water. The area to be tested is rubbed with the swab. If mercury ($Hg^{+2}$) is present, the swab turns deep blue.

Example XXXII

One crushable cartridge is filled with 30 mg of ammonium thiocyanate, cobalt (II), and an inert filler such as talc. Another breakable cartridge is filled with 0.5 ml of activator solution containing a neutral buffer or water.

The two cartridges are placed inside a larger cartridge having a swab tip at one end. When ready to use, the breakable cartridges are broken and the unit is shaken to ensure good mixing. The swab tip is rubbed over the area to be tested and becomes deep blue if mercury ($Hg^{+2}$) is present.

Example XXXIII

A swab with a hollow stem is filled with 30 mg of a mixture of Rhodamine B (tetraethylrhodamine) and sodium nitrite (as an oxidizing agent) and an inert filler such as alumina in ratios as shown in Table VI. The swab tip is wetted with an activated solution containing 15% potassium chloride in 2M HCl. The area to be tested is rubbed with the swab. If antimony as the chloroantimonate ion ($SbCl_6$) is present, the swab turns violet or blue.

Example XXXIV

One crushable cartridge is filled with 30 mg of Rhodamine B (tetraethylrhodamine) and sodium nitrite (as an oxidizing agent) and an inert filler such as talc. Another breakable cartridge is filled with 0.5 ml of activator solution containing 15% potassium chloride in 2M HCl. The two cartridges are placed inside a larger cartridge having a swab tip at one end. When ready to use, the breakable cartridges are broken and the unit is shaken to ensure good mixing. The swab tip is rubbed over the area to be tested and becomes violet or blue if antimony as the chloroantimonate ion ($SbCl_6$) is present.

Example XXXV

A swab with a hollow stem is filled with 30 mg of a mixture of phosphomolybdic acid and an inert filler such as alumina in ratios as shown in Table VI. The swab tip is wetted with an activator solution containing dilute acid such as 0.1M HCl. The area to be tested is rubbed with the swab. The tip of the swab is held over steam for a few minutes. If antimony ($Sb^{+3}$) is present, the swab turns blue.

Example XXXVI

One crushable cartridge is filled with 30 mg of phosphomolybdic acid and an inert filler such as talc. Another breakable cartridge is filled with 0.5 ml of activator solution containing dilute acid such as 0.1M HCl.

The two cartridges are placed inside a larger cartridge having a swab tip at one end. When ready to use, the breakable cartridges are broken and the unit is shaken to ensure good mixing. The swab tip is rubbed over the area to be tested and then held over a stream of steam for a few minutes. If antimony ($Sb^{+3}$) is present, the swab turns blue.

Example XXXVII

A swab with a hollow stem is filled with 30 mg of a mixture of 2,2'-bipyridine and an inert filler such as alumina in ratios as shown in Table VI. The swab tip is wetted with an activator solution containing 0.1M HCl and hydroxylamine hydrochloride as reducing agent (pH 2). The area to be tested is rubbed with the swab. If iron (II) ion is present, the swab turns pink or red. Reducing agent hydroxylamine hydrochloride is added to the activating solution to reduce ferric ions ($Fe^{+3}$) to ferrous ions ($Fe^{+2}$).

Example XXXVIII

One crushable cartridge is filled with 30 mg of 2,2'-bipyridine and an inert filler such as talc. Another breakable cartridge is filled with 0.5 ml of activator solution containing 0.1 HCl and hydroxylamine hydrochloride as reducing agent (pH 2). The two cartridges are placed inside a larger cartridge having a swab tip at one end. When ready to use, the breakable cartridges are broken and the unit is shaken to ensure good mixing. The swab tip is rubbed over the area to be tested and becomes pink or red if iron (II) ion is present.

Reducing agent hydroxylamine hydrochloride is added to the activating solution to reduce ferric ions ($Fe^{+3}$) to ferrous ions ($Fe^{+2}$).

Example XXXIX

A single crushable cartridge is filled with 0.5 ml activator solution containing 0.1M HCl and hydroxylamine hydrochloride (pH 2). The swab tip is impregnated with 2,2'-bipyridine by wetting the tip with a solution of 2,2'-bipyridine in ethanol and allowing the tip to dry.

The single cartridge is placed inside a larger cartridge having the swab tip at one end. When ready to use, the breakable cartridge is broken and the unit is squeezed gently to wet the swab tip. The swab tip is rubbed over the area to be tested and becomes pink or red if iron (II) ion is present.

Example XL

A swab with a hollow stem is filled with 30 mg of a mixture of o-phenanthroline and an inert filler such as alumina in ratios as shown in Table VI. The swab tip is wetted with an activator solution containing 0.1M HCl and hydroxylamine hydrochloride as reducing agent (pH 2). The area to be tested is rubbed with the swab. If iron (II) ion is present, the swab turns pink or red.

Reducing agent hydroxylamine hydrochloride is added to the activating solution to reduce ferric ions ($Fe^{+3}$) to ferrous ions ($Fe^{+2}$).

Example XLI

One crushable cartridge is filled with 30 mg of o-phenanthroline and an inert filler such as talc. Another breakable cartridge is filled with 0.5 ml of activator solution containing 0.1M HCl and hydroxylamine hydrochloride as reducing agent (pH 2). Reducing agent hydroxylamine hydrochloride is added to the activating solution to reduce ferric ions ($Fe^{+3}$) to ferrous ions ($Fe^{+2}$).

The two cartridges are placed inside a larger cartridge having a swab tip at one end. When ready to use, the breakable cartridges are broken and the unit is shaken to ensure good mixing. The swab tip is rubbed over the area to be tested and becomes pink or red if iron (II) ion is present.

Example XLII

A single crushable cartridge is filled with 0.5 ml activator solution containing 0.1M HCl and hydroxylamine hydrochloride (pH 2). The swab tip is impregnated with o-phenanthroline by wetting the tip with a solution of o-phenanthroline in water and allowing the tip to dry.

The single cartridge is placed inside a larger cartridge having the swab tip at one end. When ready to use, the breakable cartridge is broken and the unit is squeezed gently to wet the swab tip. The swab tip is rubbed over the area to be tested and becomes pink or red if iron (II) ion is present.

Example XLIII

A swab with a hollow stem is filled with 30 mg of a mixture of the iron specific reagent, 3-(2-pyridyl)-5,6-bis(4-phenylsulfonic acid)-1,2,4-triazine monosodium salt, and an inert filler such as alumina in a ratio as shown in Table VI. The swab tip is wetted with an activator solution containing water or dilute acid (0.1M HCl) or thioglycolic buffer and hydroxylamine hydrochloride as reducing reagent at pH 2. The area to be tested is rubbed with the swab. If iron (II) is present, the swab turns purple.

Example XLIV

One crushable cartridge is filled with 30 mg of the iron specific reagent 3-(2-pyridyl)-5,6-bis(4-phenylsulfonic acid)-1,2,4-triazine monosodium salt, and an inert filler such as talc. Another breakable cartridge is filled with 0.5 ml of activator solution containing water or dilute acid (0.1M HCl) or thioglycolic buffer and hydroxylamine hydrochloride as reducing reagent at pH 2.

The two cartridges are placed inside a larger cartridge having a swab tip at one end. When ready to use, the breakable cartridges are broken and the unit is shaken to ensure good mixing. The swab tip is rubbed over the area to be tested and becomes purple if iron (II) ion is present.

Example XLV

A swab with a hollow stem is filled with 30 mg of a mixture of aurine tricarboxylic acid and an inert filler such as silica in ratios as shown in Table VI. The swab tip is wetted with an activator solution containing dilute NaOH. The area to be tested is rubbed with the swab. If aluminum ion ($Al^{+3}$) is present, the swab turns red.

Example XLVI

One crushable cartridge is filled with 30 mg of a mixture of aurine tricarboxylic acid and an inert filler such as silica. Another breakable cartridge is filled with 0.5 ml of activator solution containing dilute NaOH.

The two cartridges are placed inside a larger cartridge having a swab tip at one end. When ready to use, the breakable cartridges are broken and the unit is shaken to ensure good mixing. The swab tip is rubbed over the area to be tested and becomes red if aluminum ($Al^{+3}$) is present.

Example XLVII

A swab tip is impregnated with the quinalizarin reagent by first soaking the tip in a solution containing quinalizarin and then allowing the tip to air dry. Prior to use, the swab tip is wetted with a solution of ammonium hydroxide. The area to be tested is rubbed with the swab. The swab tip is then developed by first exposing the tip to ammonia vapors and then to glacial acetic acid vapors. If aluminum ion ($Al^{+3}$) is present, the swab tip turns red to red-violet.

The quinalizarin reagent is prepared by dissolving 10 mg quinalizarin in 2 ml pyridine and diluting with 18 ml acetone.

Example XLVIII

A swab tip is impregnated with the quinalizarin reagent by first soaking the tip in a solution containing quinalizarin and then allowing the tip to air dry. One crushable cartridge (labelled A) is filled with 0.3 ml of concentrated ammonia solution. Another breakable cartridge (labelled B) is filled with 0.3 ml of glacial acetic acid.

The two cartridges are placed inside a larger cartridge having the quinalizarin impregnated swab tip at one end. When ready to use, the crushable cartridge (A) containing the ammonia is broken first and the unit is gently squeezed to wet the swab tip. The swab tip is rubbed over the area to be tested. Then the second cartridge (B) containing the glacial acetic acid is broken and the unit is gently squeezed to wet the tip with the acid. If aluminum ion ($Al^{+3}$) is present, the swab tip develops a red to red-violet color.

The quinalizarin reagent is prepared by dissolving 10 mg quinalizarin in 2 ml pyridine and diluting with 18 ml acetone.

Example XLIX

A swab with a hollow stem is filled with 30 mg of a mixture of iron (III) chloride and an inert filler such as alumina in ratios as shown in Table VI. The swab tip is first wetted with a solution containing dilute phosphoric acid adjusted to pH 4–5. The area to be tested is rubbed with the swab. Then approximately 5 drops of syrupy phosphoric acid is applied to the swab tip and allowed to soak in. Finally 2–3 drops of a developer solution containing 1% pyrrole in aldehyde-free ethanol is applied to the swab tip. If selenium ($Se^{+2}$) is present, the swab turns greenish-blue.

Example L

One crushable cartridge labelled A is filled with 0.5 ml solution of 0.5M iron (III) chloride in dilute phosphoric acid (0.1M). Another breakable cartridge labelled B is filled with 0.5 ml of developing reagent which consists of 1% pyrrole reagent in aldehyde-free ethanol. A small, separate dropper filled with concentrated phosphoric acid (sp. gr. 1.75) is also provided.

The two cartridges are placed inside a larger cartridge having a swab tip at one end. When ready to use, the breakable cartridge (labelled A) nearest the swab tip is broken first and the unit is gently squeezed to wet the swab tip. The swab tip is rubbed over the area to be tested. Then 4-5 drops of concentrated phosphoric acid (contained in dropper) is applied to the swab tip and allowed to soak in. The second breakable cartridge (labeled B) containing the developer solution is broken and the unit is gently squeezed to allow the developer solution to soak through the swab tip. If the swab tip becomes greenish blue, then selenium ion ($Se^{+2}$) or selenites are present.

Example LI

A swab with a hollow stem is filled with 30 mg of a mixture of rubeanic acid (or dithiooxamide) and an inert filler such as alumina in ratios as shown in Table VI. The swab tip is wetted with an activator solution containing ammoniacal alkali tartrates at a pH greater than 9. The area to be tested is rubbed with the swab. If copper ($Cu^{+2}$) is present, the swab turns black or greenish black. Nickel and cobalt ions also react with rubeanic acid under similar conditions to form blue and brown precipitates or colors, respectively.

Example LII

One crushable cartridge is filled with (1) 30 mg of a mixture of rubeanic acid (dithiooxamide) and an inert filler such as alumina or talc. Another breakable cartridge is filled with 0.5 ml of activator solution containing ammonia and alkali tartrates at a pH greater than 9.

The two cartridges are placed inside a larger cartridge having a swab tip at one end. When ready to use, the breakable cartridges are broken and the unit is shaken to ensure good mixing. The swab tip is rubbed over the area to be tested and becomes black to greenish black if copper ions ($Cu^{+2}$) are present. Nickel and cobalt ions also react with rubeanic acid under similar conditions to form blue and brown precipitates or color, respectively.

Example LIII

A swab with a hollow stem is filled with 30 mg of a mixture of 2,2'-biquinoline-4,4'-dicarboxylic acid or 2,2'-biquinoline (cupron) and an inert filler such as alumina in ratios as shown in Table VI. The swab tip is first wetted with 0.5 ml amyl alcohol to solubilize the cupron into the swab. The swab tip is then wetted with approximately 1 ml of an activator solution at pH 2 (see below). The area to be tested is rubbed with the swab. If copper ions ($Cu^{+2}$) are present, the swab turns purple or red.

The activator solution is prepared by dissolving 20 g sodium acetate, 10 g potassium- sodium tartrates and 3 g hydroxylammonium chloride in 100 ml water. The pH is adjusted to 2 with HCl.

Example LIV

One crushable cartridge is filled with 0.5 ml of a solution of 2,2'-biquinoline-4,4'-dicarboxylic acid or 2,2'-biquinoline (cupron) in amyl alcohol (0.2 g/l). Another breakable cartridge is filled with 0.5 ml of activator solution (see below) adjusted to pH 2.

The two cartridges are placed inside a larger cartridge having a swab tip at one end. When ready to use, the breakable cartridges are broken, and the unit is shaken to ensure good mixing and then gently squeezed to wet the swab tip. The swab tip is rubbed over the area to be tested and becomes purple or red if copper ion ($Cu^{+2}$) is present.

The activator solution is prepared by dissolving 20 g sodium acetate, 10 g potassium- sodium tartrates and 3 g hydroxylammonium chloride in 100 ml water. The pH is adjusted to 2 with HCl.

Example LV

A swab with a hollow stem is filled with 30 mg of a mixture of magnesium nitrate ($Mg(NO_3)_2$) and an inert filler such as alumina in ratios as shown in Table VI. The swab tip is first wetted with a solution containing ammonium chloride ($NH_4Cl$) and a little ammonia at a pH greater than 7. The area to be tested is rubbed with the swab. The swab tip is then wetted with the second solution containing silver nitrate in dilute acid (0.01 to 0.3M HCl). If arsenate ion ($AsO_4^{-3}$) is present, the swab turns red.

Example LVI

One crushable cartridge (labelled A) is filled with 0.5 ml of the magnesium nitrate reagent, a solution containing magnesium nitrate ($Mg(NO_3)_2$), ammonium chloride ($NH_4Cl$) and a little ammonia. Another breakable cartridge (labelled B) is filled with 0.5 ml of a solution containing silver nitrate ($Ag(NO_3)_2$) in dilute acid 0.01 to 0.3M HCl).

The two cartridges are placed inside a larger cartridge having a swab tip at one end. When ready to use, the breakable cartridge labelled A is broken first and the unit is gently squeezed to wet the swab tip. The swab tip is rubbed over the area to be tested. Then the breakable cartridge labelled B is broken and the unit is again gently squeezed to thoroughly wet the swab tip. If arsenate ions ($AsO_4^{-3}$) are present, the swab turns red.

Example LVII

One crushable cartridge (labelled A) is filled with 0.5 ml of a solution containing magnesium nitrate ($Mg(NO_3)_2$) and ammonium chloride ($NH_4Cl$). A second breakable cartridge (labelled B) is filled with ammonia (0.3 ml). A third breakable cartridge (labelled C) is filled with 0.5 ml of a solution containing silver nitrate ($Ag(NO_3)_2$) in dilute acid (0.01 to 0.3M HCl).

The three cartridges are placed inside a larger cartridge having a swab tip at one end. When ready to use, the breakable cartridges labelled A and B are broken first and the unit is gently squeezed to mix the contents and to wet the swab tip. The swab tip is rubbed over the area to be tested. Then the breakable cartridge labelled C is broken and the unit is again gently squeezed to thoroughly wet the swab tip. If arsenate ions ($AsO_4^{-3}$) are present, the swab turns red.

Example LVIII

One crushable cartridge is filled with 0.5 ml of a 7% solution of sodium sulfide. Another breakable cartridge is filled with 0.5 ml of dilute acid (0.01 -0.3M HCl).

The two cartridges are placed inside a larger cartridge having a swab tip at one end. When ready to use, the breakable cartridges are broken and the unit is shaken to ensure good mixing and gently squeezed to wet the swab tip. The swab tip is rubbed over the area to be tested and becomes black if lead ($Pb^{+2}$) ion is present.

Example LIX

One crushable cartridge is filled with 0.5 ml of a 7% solution of sodium sulfide. Another breakable cartridge is filled with 0.5 ml of dilute acid (0.01 –0.3M HCl).

The two cartridges are placed inside a larger cartridge having a swab tip at one end. When ready to use, the breakable cartridges are broken and the unit is shaken to ensure good mixing and gently squeezed to wet the swab tip. The swab tip is rubbed over the area to be tested and becomes black if mercury II ($Hg^{+2}$) ion is present.

Example LX

One crushable cartridge is filled with 0.5 ml of a 7% solution of sodium sulfide. Another breakable cartridge is filled with 0.5 ml of 1.0M HCl.

The two cartridges are placed inside a larger cartridge having a swab tip at one end. When ready to use, the breakable cartridges are broken and the unit is shaken to ensure good mixing and gently squeezed to wet the swab tip. The swab tip is rubbed over the area to be tested and becomes black if copper II ($Cu^{+2}$) ion is present.

Example LXI

One crushable cartridge is filled with 0.5 ml of a 7% solution of sodium sulfide. Another breakable cartridge is filled with 0.5 ml of dilute acid (0.3–0.5M HCl).

The two cartridges are placed inside a larger cartridge having a swab tip at one end. When ready to use, the breakable cartridges are broken and the unit is shaken to ensure good mixing and gently squeezed to wet the swab tip. The swab tip is rubbed over the area to be tested and becomes yellow if cadmium II ($Cd^{+2}$) ion is present.

Example LXII

One crushable cartridge is filled with 0.5 ml of a 7% solution of sodium sulfide. Another breakable cartridge is filled with 0.5 ml of dilute acid (0.01–0.3M HCl).

The two cartridges are placed inside a larger cartridge having a swab tip at one end. When ready to use, the breakable cartridges are broken and the unit is shaken to ensure good mixing and gently squeezed to wet the swab tip. The swab tip is rubbed over the area to be tested and becomes brown if bismuth ($Bi^{+3}$) ion is present.

Example LXIII

One crushable cartridge is filled with 0.5 ml of a 7% solution of sodium sulfide. Another breakable cartridge is filled with 0.5 ml of dilute acid (0.01–0.3M HCl).

The two cartridges are placed inside a larger cartridge having a swab tip at one end. When ready to use, the breakable cartridges are broken and the unit is shaken to ensure good mixing and gently squeezed to wet the swab tip. The swab tip is rubbed over the area to be tested and becomes brown if tin II ($Sn^{+2}$) ion is present and yellow if tin IV ($Sn^{+4}$) ion is present.

Example LXIV

One crushable cartridge is filled with 0.5 ml of a 7% solution of sodium sulfide. Another breakable cartridge is filled with 0.5 ml of dilute acid (0.01–0.3M HCl).

The two cartridges are placed inside a larger cartridge having a swab tip at one end. When ready to use, the breakable cartridges are broken and the unit is shaken to ensure good mixing and gently squeezed to wet the swab tip. The swab tip is rubbed over the area to be tested and becomes yellow if selenium as the selenite ion ($SeO_3^{-2}$) is present.

Example LXV

One crushable cartridge is filled with 0.5 ml of a 7% solution of ammonium sulfide. Another breakable cartridge is filled with 0.5 ml of an ammoniacal solution.

The two cartridges are placed inside a larger cartridge having a swab tip at one end. When ready to use, the breakable cartridges are broken and the unit is shaken to ensure good mixing and gently squeezed to wet the swab tip. The swab tip is rubbed over the area to be tested and becomes black if either iron II ($Fe^{+2}$) or iron III ($Fe^{+3}$) ions are present. The black precipitate can turn brown on oxidation in air.

Example LXVI

One crushable cartridge is filled with 0.5 ml of a 7% solution of ammonium sulfide. Another breakable cartridge is filled with 0.5 ml of 0.1M NaOH. The swab tip is dyed blue or any dark color.

The two cartridges are placed inside a larger cartridge having the blue swab tip at one end. When ready to use, the breakable cartridges are broken and the unit is shaken to ensure good mixing and gently squeezed to wet the swab tip. The swab tip is rubbed over the area to be tested and becomes white if aluminum ion ($Al^{+3}$) is present.

Example LXVII

One crushable cartridge is filled with 0.5 ml of a 7% solution of ammonium sulfide. Another breakable cartridge is filled with 0.5 ml of concentrated HCl. A third breakable cartridge is filled with a small crystal of iodine to act as a catalyst.

The three cartridges are placed inside a larger cartridge having a swab tip at one end. When ready to use, the breakable cartridges are broken and the unit is shaken to ensure good mixing and gently squeezed to wet the swab tip. The swab tip is rubbed over the area to be tested and becomes yellow if arsenic ions ($As^{+3}$ or $As^{+5}$) are present.

Example LXVIII

A swab with a hollow stem is filled with 30 mg of a mixture of copper sulfate and an inert filler such as silica in ratios as shown in Table VI. The swab tip is wetted with an activator solution containing neutral buffer such as 0.1M potassium phosphate at pH 7.0. The area to be tested is rubbed with the swab. If selenium as the selenite ion ($SeO_3^{-2}$) is present, the swab turns bluish-green.

Example LXIX

One crushable cartridge is filled with 30 mg of copper sulfate and an inert filler such as talc. Another breakable cartridge is filled with 0.5 ml of activator solution containing a neutral buffer such as 0.1M potassium phosphate adjusted to pH 7.0.

The two cartridges are placed inside a larger cartridge having a swab tip at one end. When ready to use, the breakable cartridges are broken and the unit is shaken to ensure good mixing. The swab tip is rubbed over the area to be tested and becomes bluish-green if selenium as the selenite ion ($SeO_3^{-2}$) is present.

Example LXX

One crushable cartridge is filled with a 0.1% solution of copper sulfate in a neutral buffer (0.1M potassium phosphate adjusted to pH 7.0). When ready to use, the breakable cartridge is broken and the unit is gently squeezed to wet the swab tip. The swab tip is rubbed over the area to be tested and becomes bluish-green if selenium as the selenite ion ($SeO_3^{-2}$) is present.

Although only preferred embodiments are specifically illustrated and described herein, it will be appreciated that many modifications and variations of the present invention are possible in light of the above teachings and within the purview of the appended claims without departing from the spirit and intended scope of the invention.

What is claimed is:

1. A swab device for testing for a metal on a surface, comprising:
    a stem;
    an absorbent ball of material mounted at one end of the stem; and
    a reagent that reacts with the metal in such a manner so as to give a visual indication of the reaction, said reagent being impregnated in the absorbent ball of material, and said metal selected from the group consisting of lead, cadmium, bismuth, mercury, cobalt, arsenic, tin, antimony, iron, selenium, and copper.

2. The device according to claim 1, wherein the metal is lead.

3. The device according to claim 1, wherein the metal is cadmium.

4. The device according to claim 1, wherein the metal is bismuth.

5. The device according to claim 1, wherein the metal is mercury.

6. The device according to claim 1, wherein the metal is cobalt.

7. The device according to claim 1, wherein the metal is arsenic.

8. The device according to claim 1, wherein the metal is tin.

9. The device according to claim 1, wherein the metal is antimony.

10. The device according to claim 1, wherein the metal is iron.

11. The device according to claim 1, wherein the metal is selenium.

12. The device according to claim 1, wherein the metal is copper.

13. The device according to claim 1, wherein the absorbent ball of material is fibrous.

14. A swab device for testing for a metal on a surface, comprising:
    a hollow stem;
    an absorbent ball of material mounted at one end of the stem;
    a passageway interconnecting an interior of said hollow stem with said absorbent ball of material;
    a first crushable cartridge within said stem interior;
    a second crushable cartridge within said first crushable cartridge;
    a reagent that reacts with the metal in such a manner so as to give a visual indication of the reaction, said reagent being located within one of the first and second crushable cartridges; and
    an activator solution for activating the metal, said activator solution being located in the other of said first and second crushable cartridges.

15. The swab device of claim 14, wherein said absorbent ball of material is fibrous.

16. The swab device of claim 14, wherein said metal is lead.

17. The swab device of claim 14, wherein said metal is mercury.

18. The swab device of claim 14, wherein said metal is cadmium.

19. The swab device of claim 14, wherein said metal is selected from the group consisting of bismuth, cobalt, arsenic, tin, antimony, iron, selenium, and copper.

20. A method of testing for a metal on a surface, comprising the steps of:
    providing a swab stick having a stem and an absorbent ball of material at one end of the stem, wherein the absorbent ball of material is impregnated with an activating solution that reacts with the metal;
    contacting the impregnated absorbent ball of material with the surface;
    impregnating the absorbent ball of material with a reagent that reacts with the metal in such a manner so as to give a visual indication of the reaction;
    detecting the presence of the metal by inspecting the impregnated ball of material for the visual indication;
    wherein the metal is selected from the group consisting of lead, cadmium, mercury, bismuth, cobalt, arsenic, tin, antimony, iron, selenium, and copper.

21. The method of claim 20, wherein said absorbent ball of material is fibrous.

22. The method of claim 20, wherein said metal is lead.

23. The method of claim 20, wherein said metal is mercury.

24. The method of claim 20, wherein said metal is cadmium.

* * * * *